US009532131B2

(12) United States Patent
Dusan et al.

(10) Patent No.: US 9,532,131 B2
(45) Date of Patent: Dec. 27, 2016

(54) SYSTEM AND METHOD OF IMPROVING VOICE QUALITY IN A WIRELESS HEADSET WITH UNTETHERED EARBUDS OF A MOBILE DEVICE

(71) Applicant: Apple Inc., Cupertino, CA (US)

(72) Inventors: Sorin V. Dusan, San Jose, CA (US); Baptiste P. Paquier, Saratoga, CA (US); Aram M. Lindahl, Menlo Park, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 14/187,187

(22) Filed: Feb. 21, 2014

(65) Prior Publication Data

US 2015/0245129 A1 Aug. 27, 2015

(51) Int. Cl.

| | |
|---|---|
| ***A61F 11/06*** | (2006.01) |
| ***H04R 1/10*** | (2006.01) |
| ***G10L 21/0208*** | (2013.01) |
| ***G10K 11/178*** | (2006.01) |
| *H04R 5/033* | (2006.01) |
| *H04R 3/00* | (2006.01) |
| *G10L 21/0216* | (2013.01) |

(52) U.S. Cl.

CPC ......... *H04R 1/1083* (2013.01); *G10K 11/1788* (2013.01); *G10L 21/0208* (2013.01); *G10L 2021/02161* (2013.01); *H04R 3/005* (2013.01); *H04R 5/033* (2013.01); *H04R 2420/07* (2013.01); *H04R 2460/13* (2013.01)

(58) Field of Classification Search

None

See application file for complete search history.

(56) References Cited

U.S. PATENT DOCUMENTS

| | | | | |
|---|---|---|---|---|
| 7,844,311 | B2 | 11/2010 | Kim | |
| 2006/0120540 | A1 * | 6/2006 | Luo | 381/98 |
| 2009/0154739 | A1 | 6/2009 | Zellner | |
| 2010/0061568 | A1 * | 3/2010 | Rasmussen | 381/94.1 |

(Continued)

FOREIGN PATENT DOCUMENTS

| | | |
|---|---|---|
| EP | 1887832 | 2/2008 |

*Primary Examiner* — Muhammad N Edun

(74) *Attorney, Agent, or Firm* — Blakely, Sokoloff, Taylor & Zafman LLP

(57) ABSTRACT

Method of improving voice quality using a wireless headset with untethered earbuds starts by receiving first acoustic signal from first microphone included in first untethered earbud and receiving second acoustic signal from second microphone included in second untethered earbud. First inertial sensor output is received from first inertial sensor included in first earbud and second inertial sensor output is received from second inertial sensor included in second earbud. First earbud processes first noise/wind level captured by first microphone, first acoustic signal and first inertial sensor output and second earbud processes second noise/wind level captured by second microphone, second acoustic signal, and second inertial sensor output. First and second noise/wind levels and first and second inertial sensor outputs are communicated between the earbuds. First earbud transmits first acoustic signal and first inertial sensor output when first noise and wind level is lower than second noise/wind level. Other embodiments are described.

28 Claims, 8 Drawing Sheets

(56) References Cited

U.S. PATENT DOCUMENTS

| | | | |
|---|---|---|---|
| 2010/0135500 A1 | 6/2010 | Derleth et al. | |
| 2012/0058727 A1 | 3/2012 | Cook et al. | |
| 2012/0230510 A1 | 9/2012 | Dinescu et al. | |
| 2013/0170665 A1 | 7/2013 | Wise et al. | |
| 2013/0287219 A1 | 10/2013 | Hendrix et al. | |
| 2013/0316642 A1 | 11/2013 | Newham | |
| 2015/0121347 A1* | 4/2015 | Petit et al. | 717/126 |

* cited by examiner

SYSTEM AND METHOD OF IMPROVING VOICE QUALITY IN A WIRELESS HEADSET WITH UNTETHERED EARBUDS OF A MOBILE DEVICE

FIELD

An embodiment of the invention relate generally to a system and method of improving the speech quality in a wireless headset with untethered earbuds of an electronic device (e.g., mobile device) by determining which of the earbuds should transmit the acoustic signal and the inertial sensor output to the mobile device. In one embodiment, the determination is based on at least one of: a noise and wind level captured by the microphones in each earbud, the inertial sensor output from the inertial sensors in each earbud, the battery level of each earbud, and the position of the earbuds.

BACKGROUND

Currently, a number of consumer electronic devices are adapted to receive speech via microphone ports or headsets. While the typical example is a portable telecommunications device (mobile telephone), with the advent of Voice over IP (VoIP), desktop computers, laptop computers and tablet computers may also be used to perform voice communications.

When using these electronic devices, the user also has the option of using the speakerphone mode or a wired headset to receive his speech. However, a common complaint with these hands-free modes of operation is that the speech captured by the microphone port or the headset includes environmental noise such as secondary speakers in the background or other background noises. This environmental noise often renders the user's speech unintelligible and thus, degrades the quality of the voice communication.

Another hands-free option includes wireless headsets to receive user's speech as well as perform playback to the user. However, the current wireless headsets also suffer from environmental noise, battery constraints, and uplink and downlink bandwidth limitations.

SUMMARY

Generally, the invention relates to improving the voice sound quality in a wireless headset with untethered earbuds of electronic devices by determining which of the earbuds should transmit the acoustic signal and the inertial sensor output to the mobile device. Specifically, the determination may be based on at least one of: a noise and wind level captured by the microphones in each earbud, the inertial sensor output from the inertial sensors in each earbud, the battery level of each earbud, and the position of the earbuds. Further, using the acoustic signal and the inertial sensor output received from one of the earbuds, user's voice activity may be detected to perform noise reduction and generate a pitch estimate to improve the speech quality of the final output signal.

In one embodiment, a method of improving voice quality of an electronic device (e.g., a mobile device) using a wireless headset with untethered earbuds starts by receiving a first acoustic signal from a first microphone included in a first untethered earbud and receiving a second acoustic signal from a second microphone included in a second untethered earbud. A first inertial sensor output from a first inertial sensor included in the first earbud and a second inertial sensor output from a second inertial sensor included in the second earbud are then received. The first and second inertial sensors may detect vibration of the user's vocal chords modulated by the user's vocal tract based on vibrations in bones and tissue of the user's head. The first earbud then processes a first noise and wind level captured by the first microphone and the second earbud processes a second noise and wind level captured by the second microphone. The first earbud may also process the first acoustic signal and the first inertial sensor output and the second earbud may also process the second acoustic signal and the second inertial sensor output. The first and second noise and wind levels and the first and second inertial sensor outputs may be communicated between the first and second earbuds. When the first noise and wind level is lower than the second noise and wind level, the first earbud may transmit the first acoustic signal and the first inertial sensor output. When the second noise and wind level is lower than the first noise and wind level, the second earbud may transmit the second acoustic signal and the second inertial sensor output. When the second inertial sensor output is lower than the first inertial sensor output by a predetermined threshold, the first earbud transmits the first acoustic signal and the first inertial sensor output. When the first inertial sensor output is lower than the second inertial sensor output by the predetermined threshold, the second earbud transmits the second acoustic signal and the second inertial sensor output. In one embodiment, when the first noise and wind level is lower than the second noise and wind level and when the first inertial sensor output is lower than the second inertial sensor output by the predetermined threshold, a first battery level of the first earbud and a second battery level of the second earbud are monitored. In this embodiment, the first earbud transmits the first acoustic signal and the first inertial sensor output when the second battery level is lower than the first battery level by a predetermined percentage threshold. Similarly, the second earbud transmits the second acoustic signal and the second inertial sensor output when the first battery level is lower than the second battery level by the predetermined percentage threshold. In another embodiment, the mobile device may detect if the first earbud and the second earbud are in an in-ear position. In this embodiment, the first earbud transmits the first acoustic signal and the first inertial sensor output when the second earbud is not in the in-ear position, and the second earbud transmits the second acoustic signal and the second inertial sensor output when the first earbud is not in the in-ear position.

In another embodiment, a system for improving voice quality of a mobile device comprises a wireless headset including a first untethered earbud and a second unthetered earbud. The first earbud may include a first microphone to transmit a first acoustic signal, a first inertial sensor to generate a first inertial sensor output, a first earbud processor to process (i) a first noise and wind level captured by the first microphone, (ii) the first acoustic signal, and (iii) the first inertial sensor output, and a first communication interface, and the second earbud may include a second microphone to transmit a second acoustic signal, a second inertial sensor to generate a second inertial sensor output, a second earbud processor to process: (i) a second noise and wind level captured by the second microphone, (ii) the second acoustic signal and (iii) the second inertial sensor output, and a second communication interface. The first and second inertial sensors detect vibration of the user's vocal chords modulated by the user's vocal tract based on vibrations in bones and tissue of the user's head. The first communication interface may communicate the first noise and wind level and the first inertial sensor output to the second communication interface, and the second communication interface may communicate the second noise and wind level and the second inertial sensor output to the first communication interface. The first communication interface may also transmits the first acoustic signal and the first inertial sensor output when the first noise and wind level is lower than the second noise and wind level, and the second communication interface may also transmit the second acoustic signal and the second inertial sensor output when the second noise and wind level is lower than the first noise and wind level. The first communication interface may also transmit the first acoustic signal and the first inertial sensor output when the second inertial sensor output is lower than the first inertial sensor output by a predetermined threshold, and the second communication interface may also transmit the second acoustic signal and the second inertial sensor output when the first inertial sensor output is lower than the second inertial sensor output by the predetermined threshold.

The above summary does not include an exhaustive list of all aspects of the present invention. It is contemplated that the invention includes all systems, apparatuses and methods that can be practiced from all suitable combinations of the various aspects summarized above, as well as those disclosed in the Detailed Description below and particularly pointed out in the claims filed with the application. Such combinations may have particular advantages not specifically recited in the above summary.

BRIEF DESCRIPTION OF THE DRAWINGS

The embodiments of the invention are illustrated by way of example and not by way of limitation in the figures of the accompanying drawings in which like references indicate similar elements. It should be noted that references to "an" or "one" embodiment of the invention in this disclosure are not necessarily to the same embodiment, and they mean at least one. In the drawings.

DETAILED DESCRIPTION

In the following description, numerous specific details are set forth. However, it is understood that embodiments of the invention may be practiced without these specific details. In other instances, well-known circuits, structures, and techniques have not been shown to avoid obscuring the understanding of this description.

Figure 1:
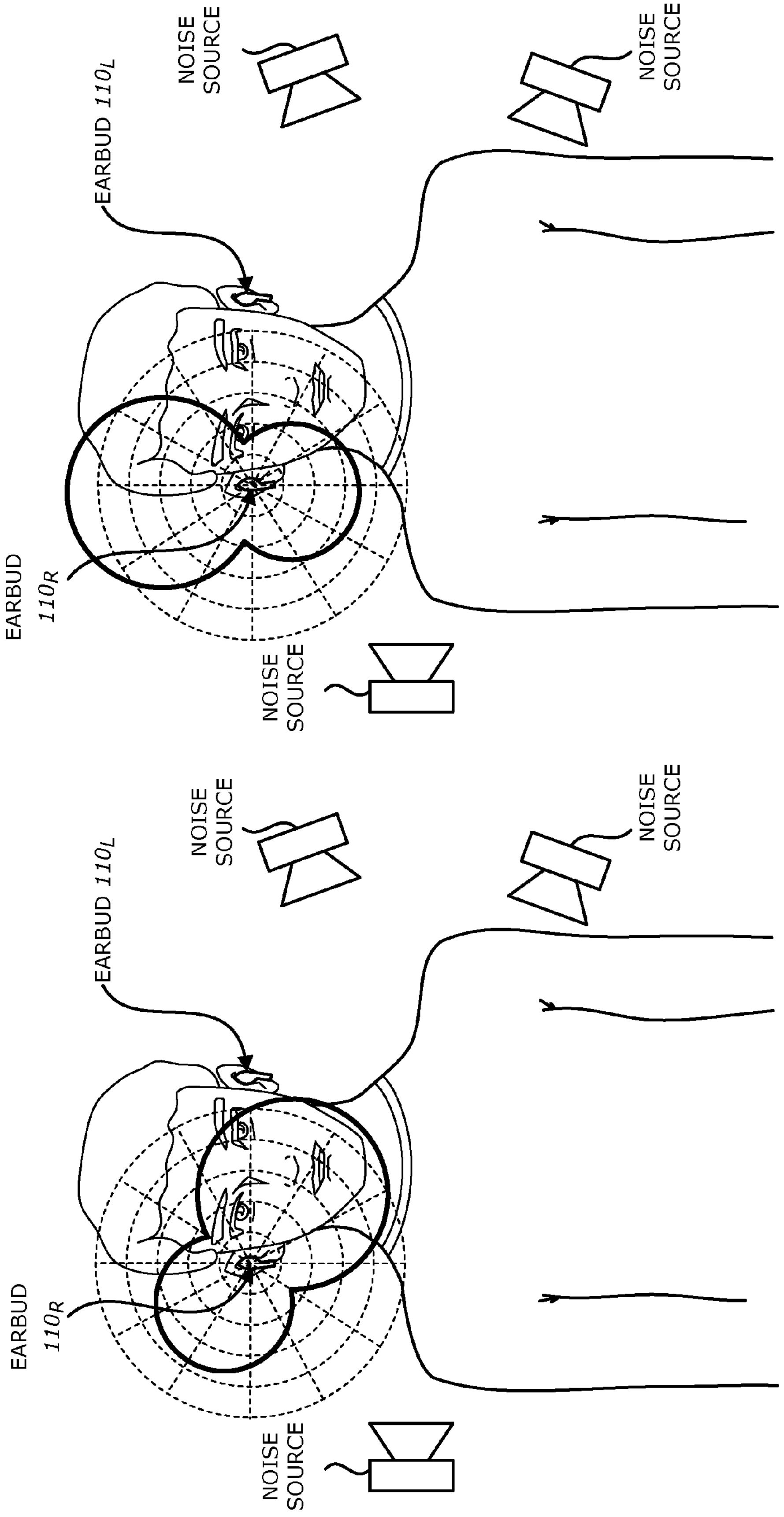
FIG. 1 illustrates an example of the wireless headset with untethered earbuds in use according to one embodiment of the invention.
Figure 2:
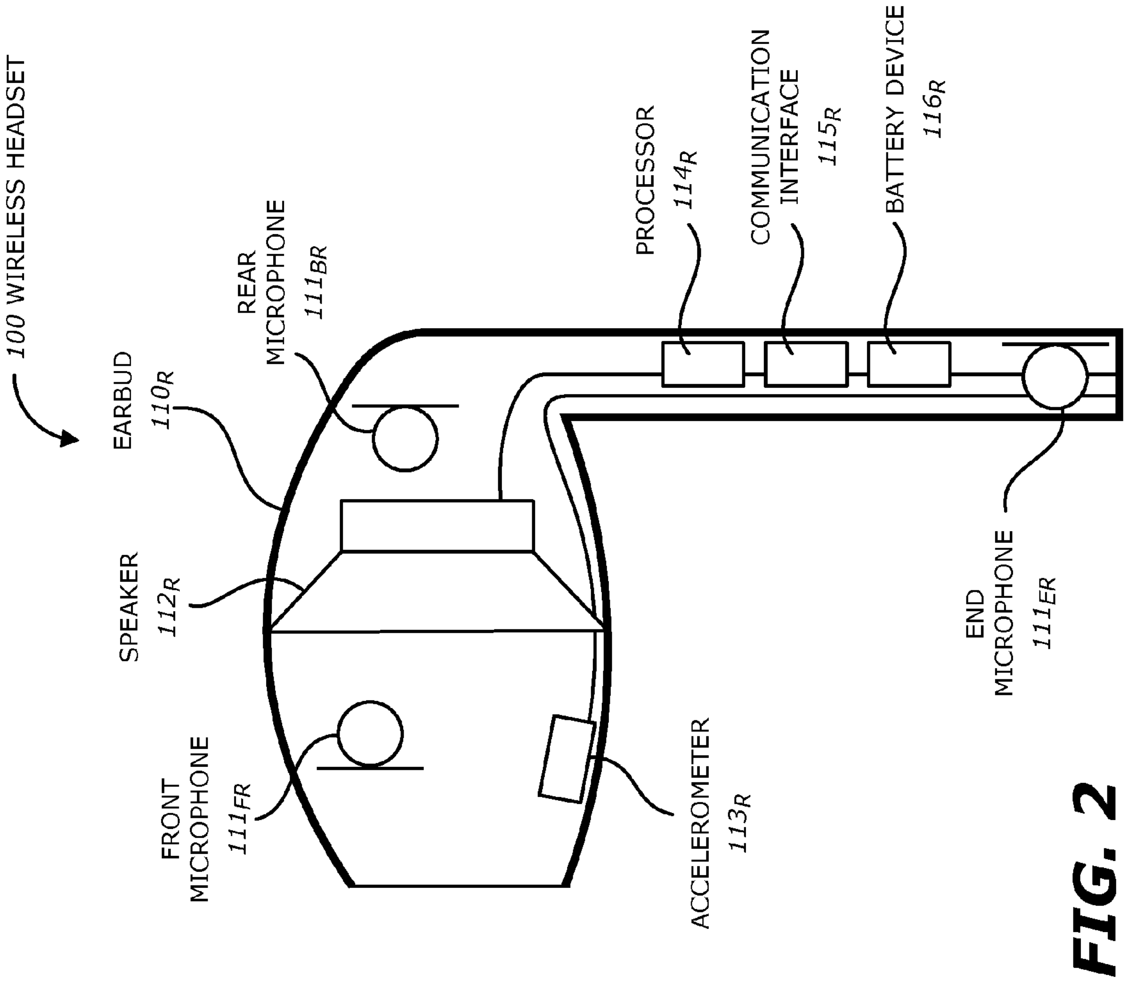
FIG. 2 illustrates an example of the right side of the headset (e.g., right untethered earbud) used with a consumer electronic device in which an embodiment of the invention may be implemented.

FIG. 1 illustrates an example of the wireless headset with untethered earbuds in use according to one embodiment of the invention. The earbuds $\mathbf{110}_L$, $\mathbf{110}_R$ work together with a consumer electronic device such as smart phone, tablet, or computer. As shown in FIG. 1, the two earbuds $\mathbf{110}_L$, $\mathbf{110}_R$ are not connected with wires to the electronic device (not shown) or between them, but communicate with each other to deliver the uplink (or recording) function and the downlink (or playback) function. FIG. 2 illustrates an example of the right side of the headset (e.g., right untethered earbud) used with the consumer electronic device in which an embodiment of the invention may be implemented. As shown in FIGS. 1 and 2, the wireless headset 100 includes a pair of untethered earbuds 110 (e.g., $\mathbf{110}_L$, $\mathbf{110}_R$). The user may place one or both the earbuds $\mathbf{110}_L$, $\mathbf{110}_R$ into his ears and the microphones $\mathbf{111}_F$, $\mathbf{111}_B$, $\mathbf{111}_E$ in the headset 100 may receive his speech. The microphones may be air interface sound pickup devices that convert sound into an electrical signal. The headset 100 in FIG. 1 is double-earpiece headset. It is understood that single-earpiece or monaural headsets may also be used. As the user is using the headset to transmit his speech, environmental noise may also be present (e.g., noise sources in FIG. 1). While the headset 100 in FIG. 2 is an in-ear type of headset that includes a pair of earbuds $\mathbf{110}_L$, $\mathbf{110}_R$ which are placed inside the user's ears, respectively, it is understood that headsets that include a pair of earcups that are placed over the user's ears may also be used. Additionally, embodiments of the invention may also use other types of headsets.

FIG. 2 illustrates an example of the right side of the headset used with a consumer electronic device in which an embodiment of the invention may be implemented. It is understood that a similar configuration may be included in the left side of the headset 100. As shown in FIG. 2, the earbud $\mathbf{110}_R$ includes a speaker $\mathbf{112}_R$, a battery device $\mathbf{116}_R$, a processor $\mathbf{114}_R$, a communication interface $\mathbf{115}_R$, a sensor detecting movement (e.g., an inertial sensor) such as an accelerometer $\mathbf{113}_R$, a front microphone $\mathbf{111}_{FR}$ that faces the direction of the eardrum, a rear (or back) microphone $\mathbf{111}_{BR}$ that faces the opposite direction of the eardrum, and an end microphone $\mathbf{111}_{EFR}$ that is located in the end portion of the earbud $\mathbf{110}_R$ where it is the closest microphone to the user's mouth. The processor $\mathbf{114}_R$ may be a digital signal processing chip that processes a noise and wind level captured by at least one of the microphones $\mathbf{111}_{FR}$, $\mathbf{111}_{BR}$, $\mathbf{111}_{ER}$, the acoustic signal from at least one of the microphones $\mathbf{111}_{FR}$, $\mathbf{111}_{BR}$, $\mathbf{111}_{ER}$ and the inertial sensor output from the accelerometer $\mathbf{113}_R$. In some embodiments, the processor $\mathbf{114}_R$ processes the noise and wind level captured by the rear microphone $\mathbf{111}_{BR}$ and the end microphone $\mathbf{111}_{ER}$ and the acoustic signal from the rear microphone $\mathbf{111}_{BR}$ and the end microphone $\mathbf{111}_{ER}$ as well. In one embodiment, the beamformers patterns illustrated in FIG. 1 are formed using the rear microphone $\mathbf{111}_{BR}$ and the end microphone $\mathbf{111}_{ER}$ to capture the user's speech (left pattern) and to capture the ambient noise (right pattern), respectively.

The communication interface $\mathbf{115}_R$ which includes a Bluetooth™ receiver and transmitter may communicate acoustic signals from the microphones $\mathbf{111}_{FR}$, $\mathbf{111}_{BR}$, $\mathbf{111}_{ER}$, and the inertial sensor output from the accelerometer $\mathbf{113}_R$ wirelessly in both directions (uplink and downlink) with the electronic device such as a smart phone, tablet, or computer. In one embodiment, the electronic device may only receive the uplink signal from one of the earbuds at a time due the channel and bandwidth limitations. In this embodiment, the communication interface 115$_R$ of the right earbud 110$_R$ may also be used to communicate wirelessly with the communication interface 115$_L$ of the left earbud 110$_L$ to determine which earbud 110$_R$, 110$_L$ is used to transmitting an uplink signal (e.g., including acoustic signals captured by the front microphone 111$_F$, the rear microphone 111$_B$, and the end microphone 111$_{ER}$ and the inertial sensor output from the accelerometer 113) to the electronic device. The earbud 110$_R$, 110$_L$ that is not used to transmit the uplink signal to the electronic device may be disabled to preserve the battery level in the battery device 116$_R$.

In one embodiment, the communication interface 115$_R$ communicates the battery level of the battery device 116$_R$ to the processor 114$_L$ and the communication interface 115$_E$ communicates the battery level of the battery device 116$_L$ to the processor 114$_R$. In this embodiment, the processors 114$_L$, 114$_R$ monitor the battery levels of the battery devices 116$_R$ and 116$_L$ and determine which earbud 110$_R$, 110$_L$ should be used to transmit the uplink signal to the electronic device based on the battery levels of the battery devices 116$_R$ and 116$_L$.

In another embodiment, the processor 114$_R$ determines whether the earbud 110$_R$ is in an in-ear position. The processor 114$_R$ may determine whether the earbud 110$_R$ is in an in-ear position based on a detection of user's speech using the inertial sensor output from the accelerometer 113$_R$. In one embodiment, to make this determination of whether the earbud is in an in-ear position, the processor 114$_R$ processes the acoustic signals from the front microphone 111$_{FR}$ and the rear microphone 111$_{BR}$ to obtain the power ratio (power of 111$_{FR}$/power of 111$_{BR}$). The power ratio may indicate whether the earbud is in an in-ear position as opposed to the out-ear position (e.g., not in the ear). In this embodiment, the signals received from the microphones 111$_{FR}$, 111$_{BR}$ are monitored to determine the in-ear position during either of the following situations: when acoustic speech signals are generated by the user or when acoustic signals are outputted from the speaker during playback.

Determining a power ratio between the front and rear microphone may include comparing the power in a specific frequency range to determine whether the front microphone power is greater than the rear microphone power by a certain percentage. The percentage (threshold) and the frequency region are dependent upon the size and shape of the earbuds and the positions of the microphones and thus may be selected based on experiments during use to provide detecting of the earbud only when the ratio displays a significant difference, such as the case when the user is speaking or when the speaker is playing audio. This method is based on the observation that when the earbud is in the ear the power ratio in a specific high frequency range is different from the power ratio in that range when the earbud is out of the ear.

If the power ratio is below a threshold, this may indicate that the earbud is not in the ear, such as when the front microphone power is nearly the same as that of the rear microphone due to both microphones not being within the user's ear. If the power ratio is above a threshold, this may indicate that the earbud is in the ear.

Some embodiments may include filtering outputs of the front and rear microphones of one earbud to pass frequencies useful for detecting a specific frequency region; then, comparing the front microphone power of the filtered front microphone output to the rear microphone power of the rear microphone output to determine a power ratio between the front and rear microphones. If the ratio is below or not greater than a predetermined percentage (e.g., a selected percentage as noted above), then determining that the one earbud is not in an ear of the user; and if the ratio is above or greater than the predetermined percentage, then determining that the one earbud is in an ear of the user. This may be repeated for the other earbud to determine if the other earbud is in the user's other ear.

In another embodiment, in order to determine the in-ear or out-ear positions of each of the earbuds 110$_L$, 110$_R$, each of the processors 114$_R$, 114$_L$ receive the inertial sensor outputs from the accelerometers 113$_R$, 113$_L$. Each of the accelerometers 113$_L$, 113$_R$ may be a sensing device that measures proper acceleration in three directions, X, Y, and Z. Accordingly, in this embodiment, each of the processors receive three (X, Y, Z directions) inertial sensor outputs from the accelerometer 113$_L$ and three (X, Y, Z directions) inertial sensor outputs from the accelerometer 113$_R$. Using these six inertial sensor outputs, the processors 114$_R$, 114$_L$ combine the six inertial sensor outputs and apply these outputs to a multivariate classifier using Gaussian Mixture Models (GMM) to determine the in-ear or out-ear positions of each of the earbuds 110$_L$, 110$_R$.

In these embodiments, the communication interface 115$_R$ transmits the acoustic signal from the microphones 111$_{FR}$, 111$_{BR}$, 111$_{ER}$, and the inertial sensor output from the accelerometer 113$_R$ when the left earbud 110$_L$ is determined to be in an out-position and/or the right earbud 110$_R$ is determined to be in an in-ear position.

The end microphone 111$_{ER}$ and the rear (or back) microphone 111$_{BR}$ may be used to create microphone array beams (i.e., beamformers) which can be steered to a given direction by emphasizing and deemphasizing selected microphones 111$_{ER}$, 111$_{BR}$. Similarly, the microphone 111$_{BR}$, 111$_{ER}$ can also exhibit or provide nulls in other given directions. Accordingly, the beamforming process, also referred to as spatial filtering, may be a signal processing technique using the microphone array for directional sound reception.

When the user speaks, his speech signals may include voiced speech and unvoiced speech. Voiced speech is speech that is generated with excitation or vibration of the user's vocal chords. In contrast, unvoiced speech is speech that is generated without excitation of the user's vocal chords. For example, unvoiced speech sounds include /s/, /sh/, /f/, etc. Accordingly, in some embodiments, both types of speech (voiced and unvoiced) are detected in order to generate an augmented voice activity detector (VAD) output which more faithfully represents the user's speech.

First, in order to detect the user's voiced speech, in one embodiment of the invention, the inertial sensor output data signal from accelerometer 113 placed in each earbud 110$_R$, 110$_L$ together with the signals from the front microphone 111$_F$, the rear microphone 111$_B$, the end microphone 111$_E$ or the beamformer may be used. The accelerometer 113 may be a sensing device that measures proper acceleration in three directions, X, Y, and Z or in only one or two directions. When the user is generating voiced speech, the vibrations of the user's vocal chords are filtered by the vocal tract and cause vibrations in the bones of the user's head which is detected by the accelerometer 113 in the earbud 110. In other embodiments, an inertial sensor, a force sensor or a position, orientation and movement sensor may be used in lieu of the accelerometer 113 in the earbud 110.

In the embodiment with the accelerometer 113, the accelerometer 113 is used to detect the low frequencies since the low frequencies include the user's voiced speech signals. For example, the accelerometer 113 may be tuned such that it is sensitive to the frequency band range that is below 2000

Hz. In one embodiment, the signals below 60 Hz-70 Hz may be filtered out using a high-pass filter and above 2000 Hz-3000 Hz may be filtered out using a low-pass filter. In one embodiment, the sampling rate of the accelerometer may be 2000 Hz but in other embodiments, the sampling rate may be between 2000 Hz and 6000 Hz. In another embodiment, the accelerometer 113 may be tuned to a frequency band range under 1000 Hz. It is understood that the dynamic range may be optimized to provide more resolution within a forced range that is expected to be produced by the bone conduction effect in the headset 100. Based on the outputs of the accelerometer 113, an accelerometer-based VAD output (VADa) may be generated, which indicates whether or not the accelerometer 113 detected speech generated by the vibrations of the vocal chords. In one embodiment, the power or energy level of the outputs of the accelerometer 113 is assessed to determine whether the vibration of the vocal chords is detected. The power may be compared to a threshold level that indicates the vibrations are found in the outputs of the accelerometer 113. In another embodiment, the VADa signal indicating voiced speech is computed using the normalized cross-correlation between any pair of the accelerometer signals (e.g. X and Y, X and Z, or Y and Z). If the cross-correlation has values exceeding a threshold within a short delay interval the VADa indicates that the voiced speech is detected. In some embodiments, the VADa is a binary output that is generated as a voice activity detector (VAD), wherein 1 indicates that the vibrations of the vocal chords have been detected and 0 indicates that no vibrations of the vocal chords have been detected.

Using at least one of the microphones in the earbud 110 (e.g., front earbud microphone $\mathbf{111}_F$, back earbud microphone $\mathbf{111}_B$, or end earbud microphone $\mathbf{111}_E$) or the output of a beamformer, a microphone-based VAD output (VADm) may be generated by the VAD to indicate whether or not speech is detected. This determination may be based on an analysis of the power or energy present in the acoustic signal received by the microphone. The power in the acoustic signal may be compared to a threshold that indicates that speech is present. In another embodiment, the VADm signal indicating speech is computed using the normalized cross-correlation between the pair of the microphone signals (e.g. front earbud microphone $\mathbf{111}_F$, back earbud microphone $\mathbf{111}_B$, end earbud microphone $\mathbf{111}_E$). If the cross-correlation has values exceeding a threshold within a short delay interval the VADm indicates that the speech is detected. In some embodiments, the VADm is a binary output that is generated as a voice activity detector (VAD), wherein 1 indicates that the speech has been detected in the acoustic signals and 0 indicates that no speech has been detected in the acoustic signals.

Both the VADa and the VADm may be subject to erroneous detections of voiced speech. For instance, the VADa may falsely identify the movement of the user or the headset 100 as being vibrations of the vocal chords while the VADm may falsely identify noises in the environment as being speech in the acoustic signals. Accordingly, in one embodiment, the VAD output (VADv) is set to indicate that the user's voiced speech is detected (e.g., VADv output is set to 1) if the coincidence between the detected speech in acoustic signals (e.g., VADm) and the user's speech vibrations from the accelerometer output data signals is detected (e.g., VADa). Conversely, the VAD output is set to indicate that the user's voiced speech is not detected (e.g., VADv output is set to 0) if this coincidence is not detected. In other words, the VADv output is obtained by applying an AND function to the VADa and VADm outputs.

Second, the signal from at least one of the microphones $\mathbf{111}_F$, $\mathbf{111}_B$, $\mathbf{111}_E$ in the earbuds $\mathbf{110}_L$, $\mathbf{110}_R$ or the output from the beamformer may be used to generate a VAD output for unvoiced speech (VADu), which indicates whether or not unvoiced speech is detected. It is understood that the VADu output may be affected by environmental noise since it is computed only based on an analysis of the acoustic signals received from a microphone in the earbuds $\mathbf{110}_L$, $\mathbf{110}_R$ or from the beamformer. In one embodiment, the signal from the microphone closest in proximity to the user's mouth or the output of the beamformer is used to generate the VADu output. In this embodiment, the VAD may apply a high-pass filter to this signal to compute high frequency energies from the microphone or beamformer signal. When the energy envelope in the high frequency band (e.g. between 2000 Hz and 8000 Hz) is above certain threshold the VADu signal is set to 1 to indicate that unvoiced speech is present. Otherwise, the VADu signal may be set to 0 to indicate that unvoiced speech is not detected. Voiced speech can also set VADu to 1 if significant energy is detected at high frequencies. This has no negative consequences since the VADv and VADu are further combined in an "OR" manner as described below.

Accordingly, in order to take into account both the voiced and unvoiced speech and to further be more robust to errors, the method may generate a VAD output by combining the VADv and VADu outputs using an OR function. In other words, the VAD output may be augmented to indicate that the user's speech is detected when VADv indicates that voiced speech is detected or VADu indicates that unvoiced speech is detected. Further, when this augmented VAD output is 0, this indicates that the user is not speaking and thus a noise suppressor may apply a supplementary attenuation to the acoustic signals received from the microphones or from beamformer in order to achieve additional suppression of the environmental noise.

The VAD output may be used in a number of ways. For instance, in one embodiment, a noise suppressor may estimate the user's speech when the VAD output is set to 1 and may estimate the environmental noise when the VAD output is set to 0. In another embodiment, when the VAD output is set to 1, one microphone array may detect the direction of the user's mouth and steer a beamformer in the direction of the user's mouth to capture the user's speech while another microphone array may steer a cardioid or other beamforming patterns in the opposite direction of the user's mouth to capture the environmental noise with as little contamination of the user's speech as possible. In this embodiment, when the VAD output is set to 0, one or more microphone arrays may detect the direction and steer a second beamformer in the direction of the main noise source or in the direction of the individual noise sources from the environment.

The latter embodiment is illustrated in FIG. 1. When the VAD output is set to 1, at least one of the microphone arrays is enabled to detect the direction of the user's mouth. The same or another microphone array creates a beamforming pattern in the direction of the user's mouth, which is used to capture the user's speech (beamformer pattern on the left part of figure). Accordingly, the beamformer outputs an enhanced speech signal. When the VAD output is either 1 or 0, the same or another microphone array may create a hypercardioid or cardioid beamforming pattern with a null in the direction of the user's mouth, which is used to capture the environmental noise. When the VAD output is 0, other microphone arrays may create beamforming patterns (not shown in FIG. 1) in the directions of individual environmental noise sources. When the VAD output is 0, the microphone arrays is not enabled to detect the direction of the user's mouth, but rather the beamformer is maintained at its previous setting. In this manner, the VAD output is used to detect and track both the user's speech and the environmental noise.

The microphones 111$_B$, 111$_E$ are generating beams in the direction of the mouth of the user in the left part of FIG. 1 to capture the user's speech and in the direction opposite to the direction of the user's mouth in the right part of FIG. 1 to capture the environmental noise. In other embodiments, the microphone 111$_F$ may also be used to generate the beams with the microphones 111$_B$, 111$_E$.

Figure 3:
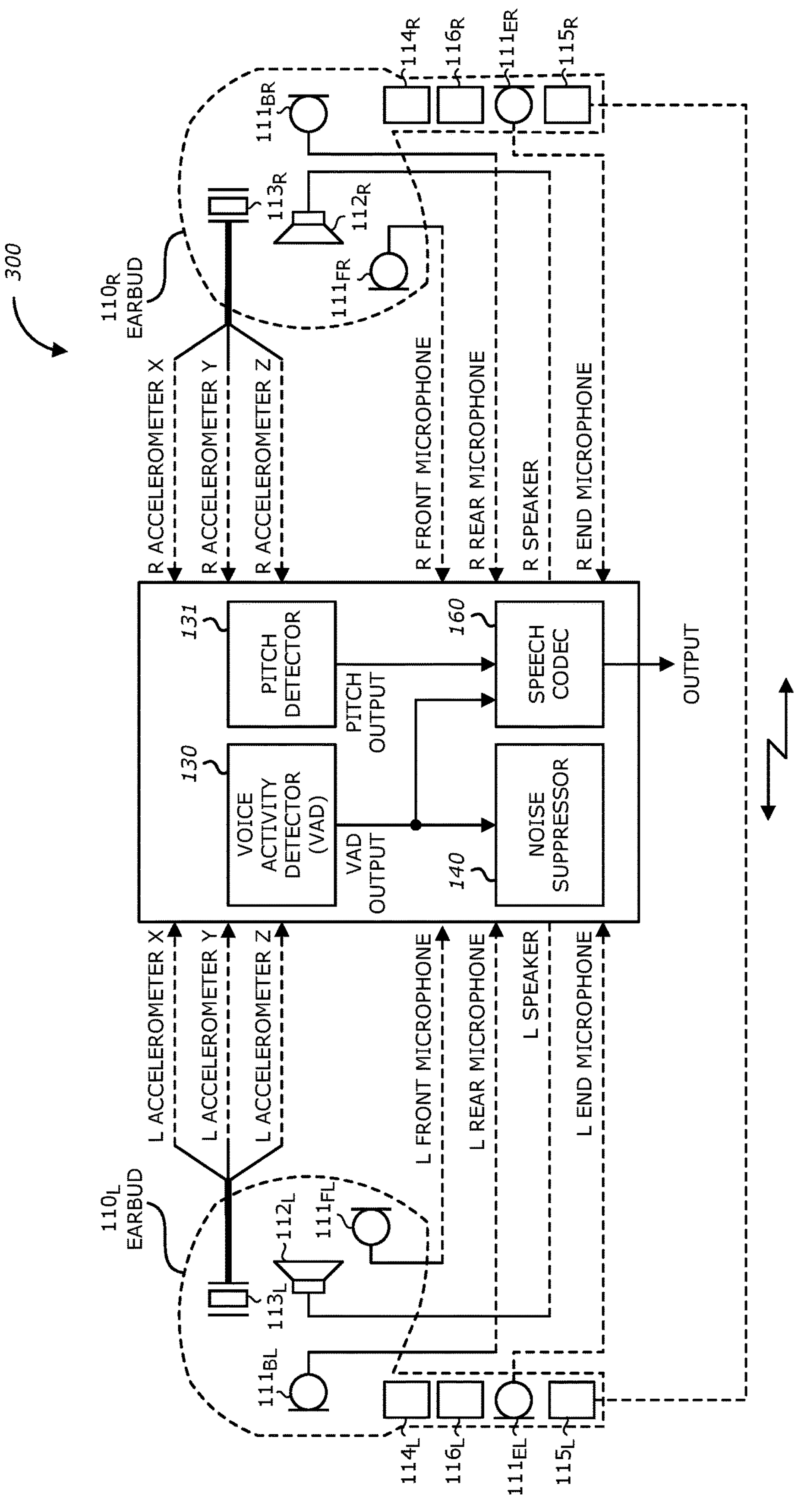
FIG. 3 illustrates a block diagram of a system for improving voice quality of a mobile device using a wireless headset with untethered earbuds according to an embodiment of the invention.

FIG. 3 illustrates a block diagram of a system for improving voice quality of a mobile device using a wireless headset with untethered earbuds according to an embodiment of the invention. The system 300 in FIG. 3 includes the wireless headset having the pair of earbuds 110$_L$, 110$_R$ and an electronic device that includes a VAD 130, a pitch detector 131, a noise suppressor 140, and a speech codec 160. In some embodiments, the system 300 also include a beamformer (not shown) that receives the acoustic signals from the microphones 111$_F$, 111$_B$, 111$_E$ from one of the earbuds 110$_L$, 110$_R$ and generates a beamformer accordingly and outputs to the noise suppressor 140.

As shown in FIG. 3, the earbuds 110$_L$, 110$_R$ are wirelessly coupled to each other and to the electronic device via the communication interfaces 115$_L$, 115$_R$. In order to determine which earbud 110$_L$, 110$_R$ will provide the uplink signals including the acoustic signals from the microphones 111$_F$, 111$_B$, 111$_E$ and the accelerometer's 113 output signals that provide information on sensed vibrations in the X, Y, and Z directions to the electronic device, the right earbud 110$_R$'s processor 114$_R$ processes the noise and wind level in the acoustic signals received from the microphones 111$_{FR}$, 111$_{BR}$ 111$_{ER}$ included in the right earbud 110$_R$, the acoustic signals received from the microphones 111$_{FR}$, 111$_{BR}$, 111$_{ER}$ and the accelerometer's 113$_R$ output signals. Similarly, the left earbud 110$_L$'s processor 114$_L$ processes the noise and wind level in the acoustic signals received from the microphones 111$_{FL}$, 111$_{BL}$ 111$_{EL}$ included in the left earbud 110$_L$, the acoustic signals received from the microphones 111$_{FL}$, 111$_{BL}$, 111$_{EL}$ and the accelerometer's 113$_L$ output signals. The earbuds 110$_L$, 110$_R$ may then communicate the respective noise and wind levels and the accelerometer output signals to each other.

In one embodiment, the earbud 110$_L$, 110$_R$ that has a lower noise and wind level transmits the uplink signals including the acoustic signals received from the microphones 111$_F$, 111$_B$, 111$_E$ and the accelerometer's 113 output signals to the electronic device. In another embodiment, the earbud 110$_L$, 110$_R$ that has the higher accelerometer 113 output (e.g., a stronger speech signal captured by the accelerometer 113) transmits the uplink signals. The earbuds 110$_L$, 110$_R$ may also communicate the battery levels in their respective battery devices 116$_L$, 116$_R$ to each other and the processor 114$_R$, 114$_L$ may also monitor the battery levels in their respective battery devices 116$_L$, 116$_R$ to determine whether the battery level of the earbud that is transmitting the uplink signals becomes smaller than the battery level of the earbud that is not transmitting the uplink signals by a given percentage. If the battery level of the transmitting earbud does become smaller than the battery level of the non-transmitting earbud by the given percentage (e.g., 10%-30%) than the non-transmitting earbud becomes the transmitting earbud and starts to transmit the uplink signals. In some embodiments, the previous transmitting earbud is disabled to preserve the remaining battery level in its battery device.

In one embodiment, if the earbud 110$_L$, 110$_R$ that has the lower noise and wind level also has the lower accelerometer 113 output (e.g., a weaker speech signal captured by the accelerometer 113), the earbud 110$_L$, 110$_R$ that has the higher battery level (or higher by a given percentage threshold) transmits the uplink signals to the electronic device.

As discussed above, the determination of which earbud 110$_L$, 110$_R$ transmits the uplink signals may be based on the processors 114$_L$, 114$_R$ determining if the earbuds 110$_L$, 110$_R$ are in an in-ear position or in an out-ear position. In this embodiment, the earbud 110$_L$, 110$_R$ does not transmit uplink signals if it is in an out-ear position.

Once one of the earbuds is selected and transmits the uplink signals to the electronic device, the VAD 130 receives the accelerometer's 113 output signals that provide information on sensed vibrations in the X, Y, and Z directions and the acoustic signals received from the microphones 111$_F$, 111$_R$, 111$_E$.

The accelerometer signals may be first pre-conditioned. First, the accelerometer signals are pre-conditioned by removing the DC component and the low frequency components by applying a high pass filter with a cut-off frequency of 60 Hz-70 Hz, for example. Second, the stationary noise is removed from the accelerometer signals by applying a spectral subtraction method for noise suppression. Third, the cross-talk or echo introduced in the accelerometer signals by the speakers in the earbuds may also be removed. This cross-talk or echo suppression can employ any known methods for echo cancellation. Once the accelerometer signals are pre-conditioned, the VAD 130 may use these signals to generate the VAD output. In one embodiment, the VAD output is generated by using one of the X, Y, Z accelerometer signals which shows the highest sensitivity to the user's speech or by adding the three accelerometer signals and computing the power envelope for the resulting signal. When the power envelope is above a given threshold, the VAD output is set to 1, otherwise is set to 0. In another embodiment, the VAD signal indicating voiced speech is computed using the normalized cross-correlation between any pair of the accelerometer signals (e.g. X and Y, X and Z, or Y and Z). If the cross-correlation has values exceeding a threshold within a short delay interval the VAD indicates that the voiced speech is detected. In another embodiment, the VAD output is generated by computing the coincidence as a "AND" function between the VADm from one of the microphone signals or beamformer output and the VADa from one or more of the accelerometer signals (VADa). This coincidence between the VADm from the microphones and the VADa from the accelerometer signals ensures that the VAD is set to 1 only when both signals display significant correlated energy, such as the case when the user is speaking. In another embodiment, when at least one of the accelerometer signal (e.g., x, y, z) indicates that user's speech is detected and is greater than a required threshold and the acoustic signals received from the microphones also indicates that user's speech is detected and is also greater than the required threshold, the VAD output is set to 1, otherwise is set to 0.

Once one of the earbuds is selected and transmits the uplink signals to the electronic device, as shown in FIG. 3, the pitch detector 131 may receive the accelerometer's 113 output signals and generate a pitch estimate based on the output signals from the accelerometer. In one embodiment, the pitch detector 131 generates the pitch estimate by using one of the X signal, Y signal, or Z signal generated by the accelerometer that has a highest power level. In this embodiment, the pitch detector 131 may receive from the accelerometer 113 an output signal for each of the three axes (i.e., X, Y, and Z) of the accelerometer 113. The pitch detector 131 may determine a total power in each of the x, y, z signals generated by the accelerometer, respectively, and select the X, Y, or Z signal having the highest power to be used to generate the pitch estimate. In another embodiment, the pitch detector 131 generates the pitch estimate by using a combination of the X, Y, and Z signals generated by the accelerometer. The pitch may be computed by using the autocorrelation method or other pitch detection methods.

For instance, the pitch detector 131 may compute an average of the X, Y, and Z signals and use this combined signal to generate the pitch estimate. Alternatively, the pitch detector 131 may compute using cross-correlation a delay between the X and Y signals, a delay between the X and Z signals, and a delay between the Y and Z signals, and determine a most advanced signal from the X, Y, and Z signals based on the computed delays. For example, if the X signal is determined to be the most advanced signal, the pitch detector 131 may delay the remaining two signals (e.g., Y and Z signals). The pitch detector 131 may then compute an average of the most advanced signal (e.g., X signal) and the delayed remaining two signals (Y and Z signals) and use this combined signal to generate the pitch estimate. The pitch may be computed by using the autocorrelation method or other pitch detection methods. As shown in FIG. 3, the pitch estimate is outputted from the pitch detector 131 to the speech codec 160.

Referring to FIG. 3, the noise suppressor 140 receives and uses the VAD output to estimate the noise from the vicinity of the user and remove the noise from the signals captured by the microphones $\mathbf{111}_F$, $\mathbf{111}_R$, $\mathbf{111}_E$ in the earbud 110. By using the data signals outputted from the accelerometers 113 further increases the accuracy of the VAD output and hence, the noise suppression. Since the acoustic signals received from the microphones $\mathbf{111}_F$, $\mathbf{111}_R$, $\mathbf{111}_E$ may wrongly indicate that speech is detected when, in fact, environmental noises including voices (i.e., distractors or second talkers, noise and wind) in the background are detected, the VAD 130 may more accurately detect the user's voiced speech by looking for coincidence of vibrations of the user's vocal chords in the data signals from the accelerometers 113 when the acoustic signals indicate a positive detection of speech. The noise suppressor 140 may output a noise suppressed speech output to the speech codec 160. The speech codec 160 may also receive the pitch estimate that is outputted from the pitch detector 131 as well as the VAD output from the VAD 130. The speech codec 160 may correct a pitch component of the noise suppressed speech output from the noise suppressor 150 using the VAD output and the pitch estimate to generate an enhanced speech final output.

The following embodiments of the invention may be described as a process, which is usually depicted as a flowchart, a flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed. A process may correspond to a method, a procedure, etc.

Figure 4:
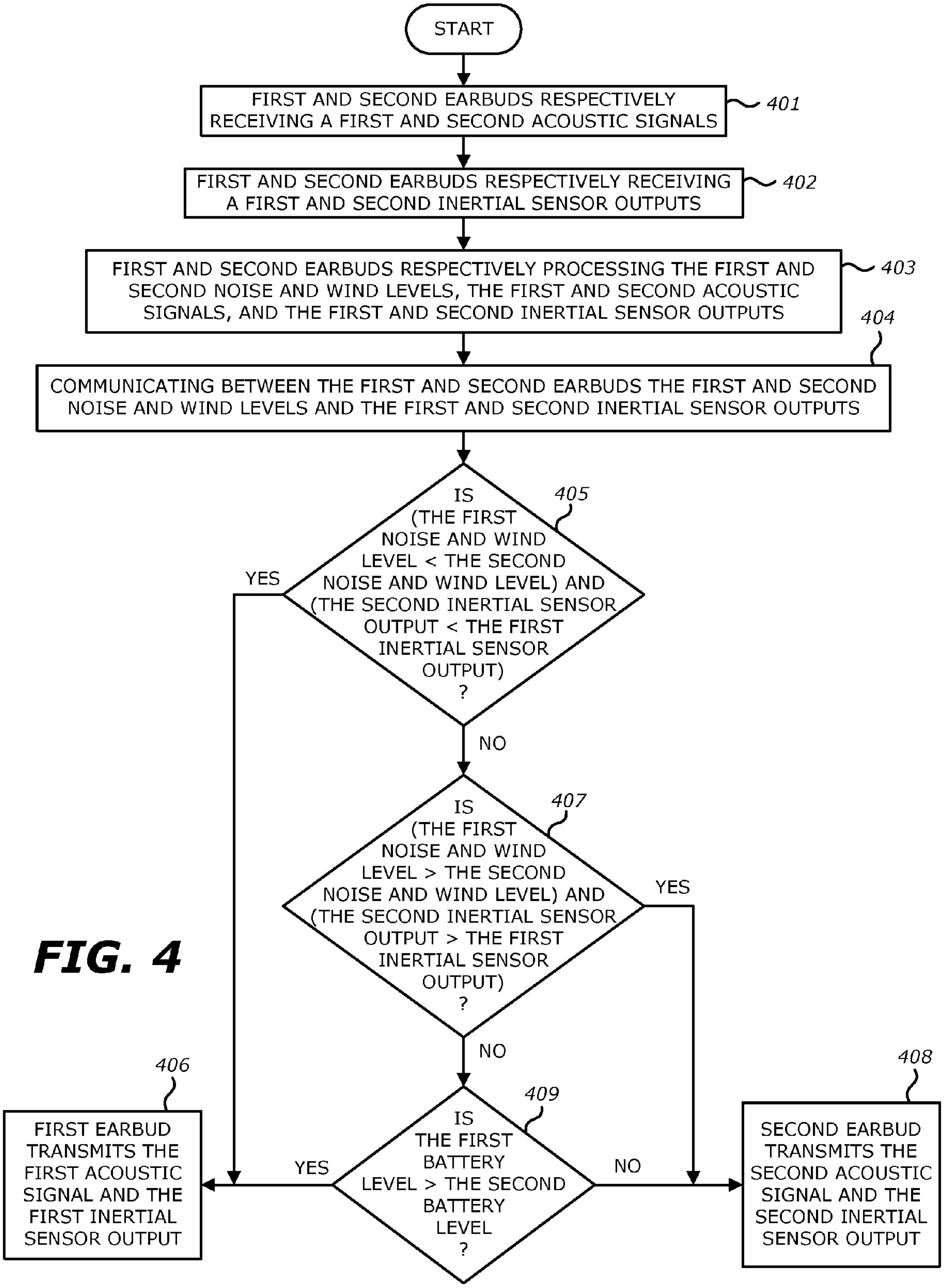
FIG. 4 illustrates a flow diagram of an example method of improving voice quality of a mobile device using a wireless headset with untethered earbuds according to an embodiment of the invention.

FIG. 4 illustrates a flow diagram of an example method of improving voice quality of a mobile device using a wireless headset with untethered earbuds according to an embodiment of the invention. Method 400 starts at Block 401 with the first (or right) and second (or left) earbuds respectively receiving the first and second acoustic signals. The first acoustic signal including the acoustic signals received from the end and rear microphones $\mathbf{111}_{ER}$, $\mathbf{111}_{BR}$ included in the right earbud $\mathbf{110}_R$ and the second acoustic signal including the acoustic signals received from the end and rear microphones $\mathbf{111}_{EL}$, $\mathbf{111}_{BL}$ included in the left earbud $\mathbf{110}_L$. In some embodiments, the first and second acoustic signals may also respectively include the acoustic signal received from the front microphones $\mathbf{111}_{FR}$, $\mathbf{111}_{FL}$. At Block 402, the first and second earbuds respectively receive the first and second inertial sensor (or accelerometer 113) outputs $\mathbf{113}_R$, $\mathbf{113}_L$. At Block 403, the first and second earbuds respectively process the first and second noise and wind levels captured by their respective end and back microphones ($\mathbf{111}_{ER}$, $\mathbf{111}_{BR}$) ($\mathbf{111}_{EL}$, $\mathbf{111}_{BL}$), the first and second acoustic signals, and the first and second inertial sensor outputs. In some embodiments, the first and second noise and wind levels may also be captured by their respective front microphones $\mathbf{111}_{FR}$, $\mathbf{111}_{FL}$. At Block 404, the first and second noise and wind levels and the first and second inertial sensor outputs are communicated between the first and second earbuds. At Block 405, a determination is made if the first noise and wind level is lower than the second noise and wind level and if the second inertial sensor output is lower than the first inertial sensor output. If both the conditions at Block 405 are met, the first earbud transmits the first acoustic signal and the first inertial sensor output (e.g., the uplink signal) (Block 406). If both the conditions at Block 405 are not met, the method continues to Block 407 where a determination is made if the first noise and wind level is higher than the second noise and wind level and if the second inertial sensor output is higher than the first inertial sensor output. If both the conditions at Block 407 are met, the second earbud transmits the second acoustic signal and the second inertial sensor output (Block 408). If both the conditions at Block 407 are not met, the method continues to Block 409, where a determination of whether the first battery level is greater than the second battery level. If at Block 409, the first battery is greater than the second battery lever, the first earbud transmits the first acoustic signal and the first inertial sensor output (Block 406) but if at Block 409, the first battery is less than the second battery lever, the second earbud transmits the second acoustic signal and the second inertial sensor output (Block 408).

In another embodiment, when both the conditions at Block 405 are met, the first battery level is checked to determine whether the first battery level is greater than a given minimum threshold level (e.g., greater than 5%-20%). In this embodiment, if the first battery level is greater than the given minimum threshold level, the method continues to Block 406 and the first earbud is used to transmit the first acoustic signal and the first inertial sensor output, otherwise the method continues to either block 408 or block 406 which has the highest battery level. Similarly, in one embodiment, when both the conditions at Block 407 are met, the second battery level is checked to determine whether the second battery level is greater than a given minimum threshold level (e.g., greater than 5%-20%). In this embodiment, if the second battery level is greater than the given minimum threshold level, the method continues to Block 408 and the second earbud is used to transmit the first acoustic signal and the first inertial sensor output, otherwise the method continues to either block 406 or block 408 which has the highest battery level.

Figure 5:
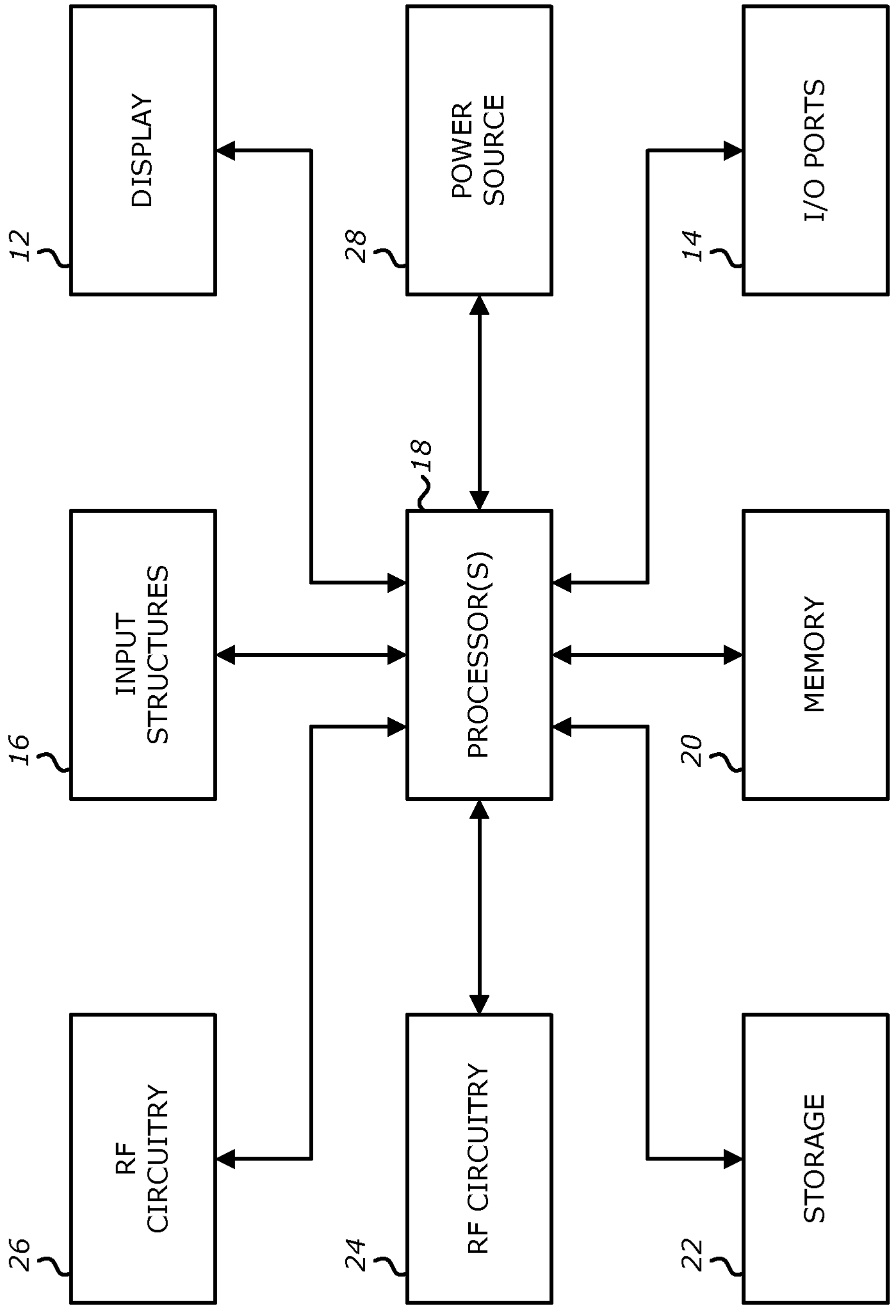
FIG. 5 is a block diagram of exemplary components of an electronic device detecting a user's voice activity in accordance with aspects of the present disclosure.
Figure 6:
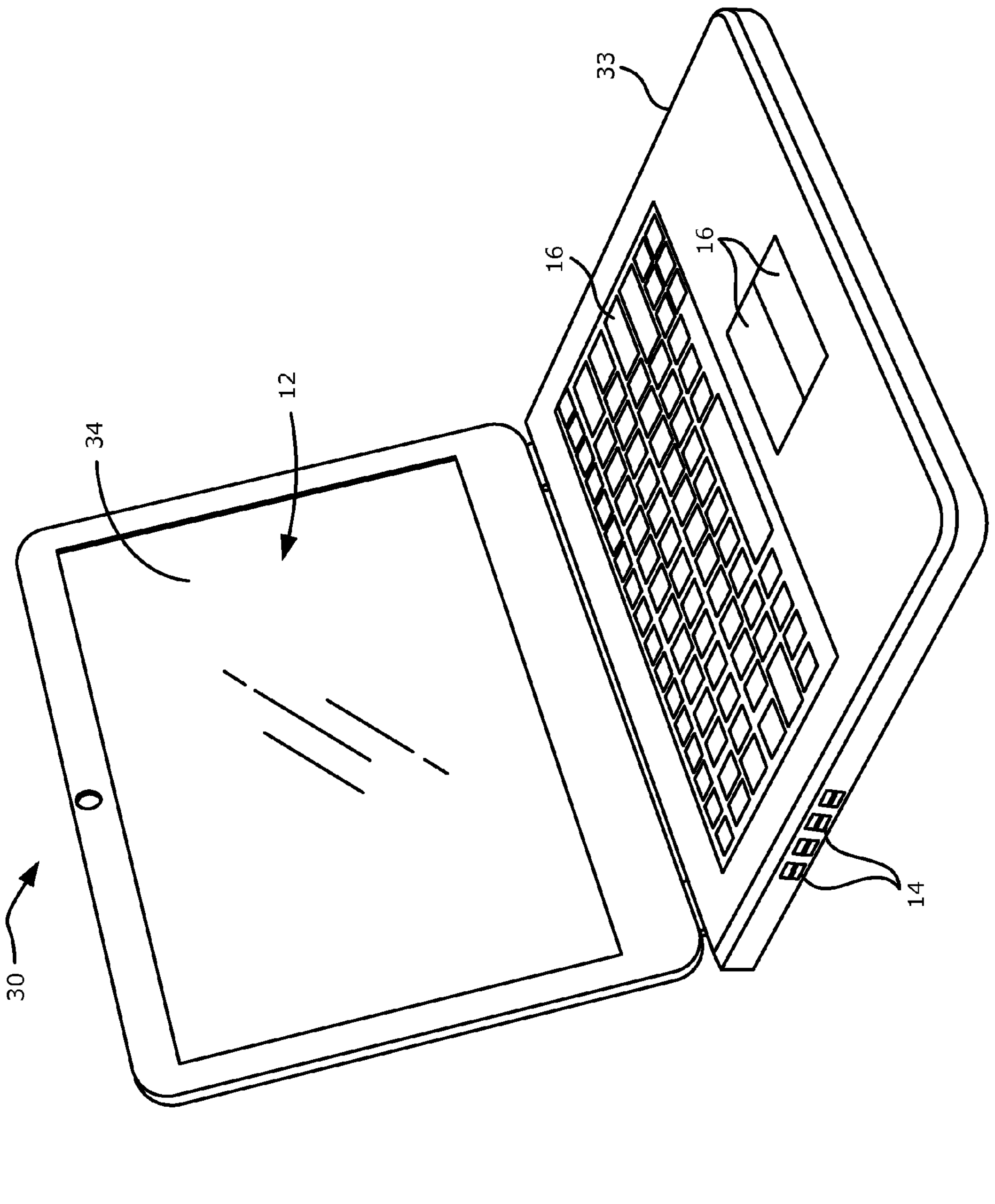
FIG. 6 is a perspective view of an electronic device in the form of a computer, in accordance with aspects of the present disclosure.
Figure 7:
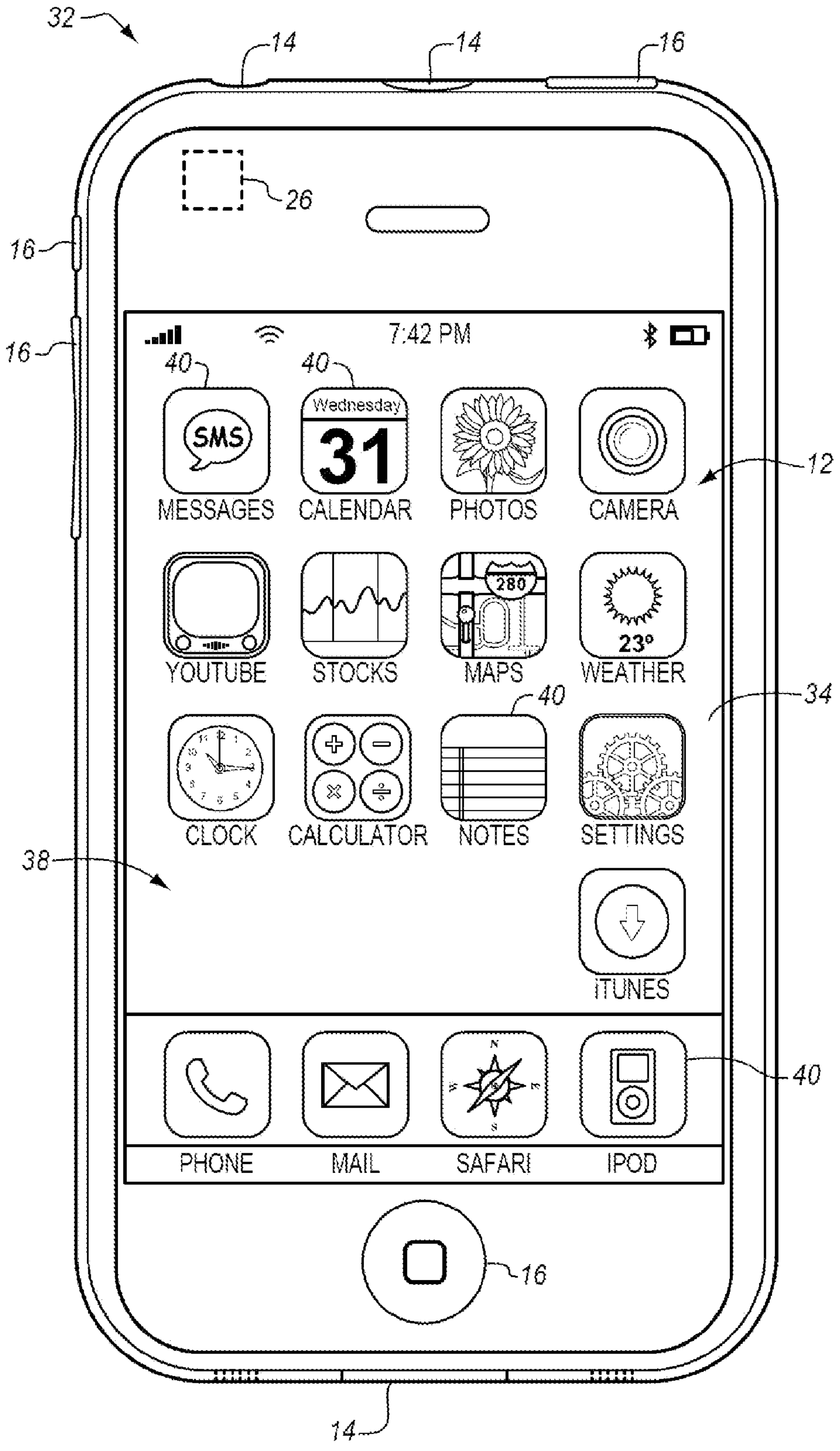
FIG. 7 is a front-view of a portable handheld electronic device, in accordance with aspects of the present disclosure.
Figure 8:
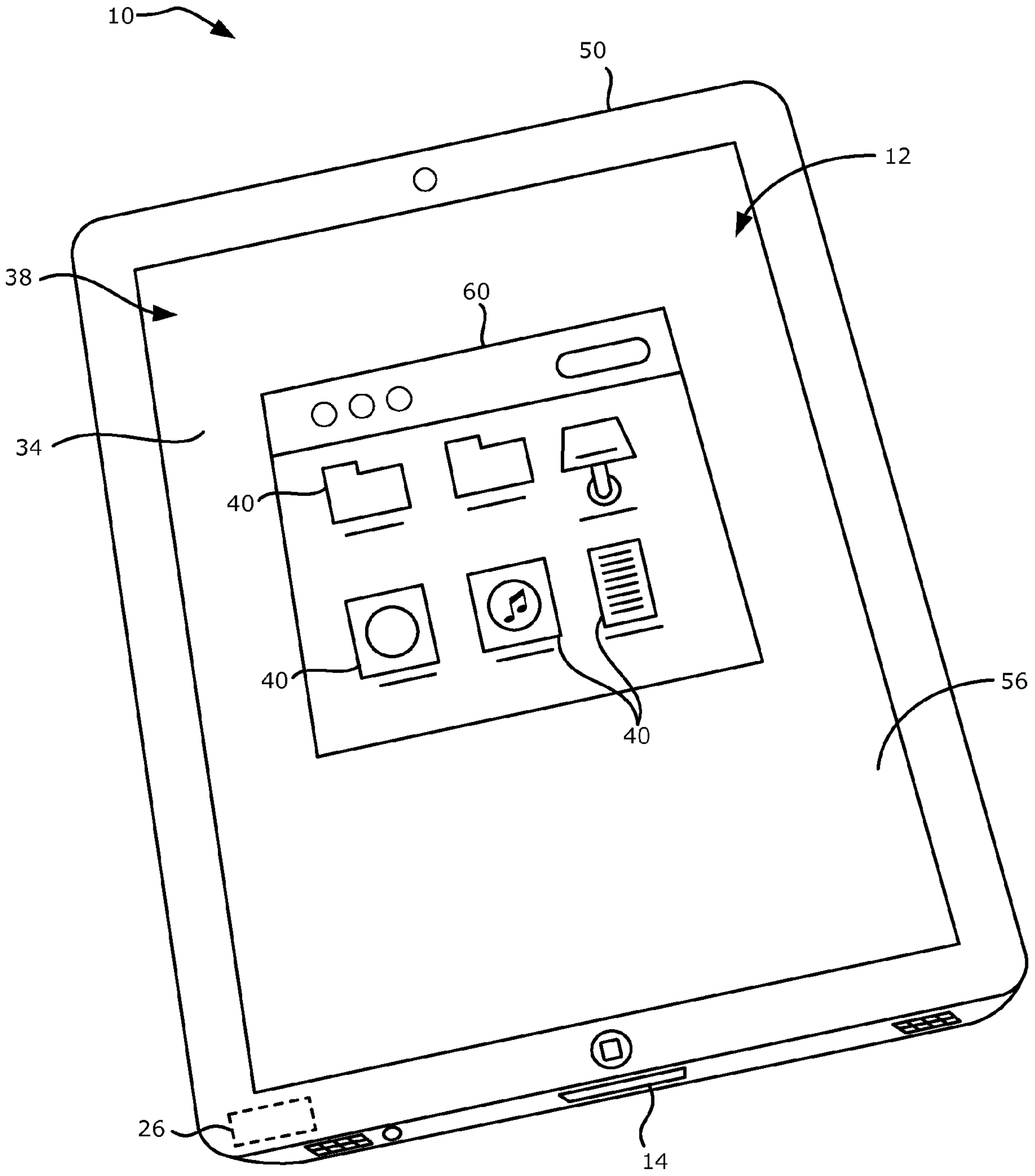
FIG. 8 is a perspective view of a tablet-style electronic device that may be used in conjunction with aspects of the present disclosure.

A general description of suitable electronic devices for performing these functions is provided below with respect to FIGS. 5-8. Specifically, FIG. 5 is a block diagram depicting various components that may be present in electronic devices suitable for use with the present techniques. FIG. 6 depicts an example of a suitable electronic device in the form of a computer. FIG. 7 depicts another example of a suitable electronic device in the form of a handheld portable electronic device. Additionally, FIG. 8 depicts yet another example of a suitable electronic device in the form of a computing device having a tablet-style form factor. These types of electronic devices, as well as other electronic devices providing comparable voice communications capabilities (e.g., VoIP, telephone communications, etc.), may be used in conjunction with the present techniques.

Keeping the above points in mind, FIG. 5 is a block diagram illustrating components that may be present in one such electronic device 10, and which may allow the device 10 to function in accordance with the techniques discussed herein. The various functional blocks shown in FIG. 5 may include hardware elements (including circuitry), software elements (including computer code stored on a computer-readable medium, such as a hard drive or system memory), or a combination of both hardware and software elements. It should be noted that FIG. 5 is merely one example of a particular implementation and is merely intended to illustrate the types of components that may be present in the electronic device 10. For example, in the illustrated embodiment, these components may include a display 12, input/output (I/O) ports 14, input structures 16, one or more processors 18, memory device(s) 20, non-volatile storage 22, expansion card(s) 24, RF circuitry 26, and power source 28.

FIG. 6 illustrates an embodiment of the electronic device 10 in the form of a computer 30. The computer 30 may include computers that are generally portable (such as laptop, notebook, tablet, and handheld computers), as well as computers that are generally used in one place (such as conventional desktop computers, workstations, and servers). In certain embodiments, the electronic device 10 in the form of a computer may be a model of a MacBook™, MacBook™ Pro, MacBook Air™, iMac™, Mac Mini, or Mac Pro™, available from Apple Inc. of Cupertino, Calif. The depicted computer 30 includes a housing or enclosure 33, the display 12 (e.g., as an LCD 34 or some other suitable display), I/O ports 14, and input structures 16.

The electronic device 10 may also take the form of other types of devices, such as mobile telephones, media players, personal data organizers, handheld game platforms, cameras, and/or combinations of such devices. For instance, as generally depicted in FIG. 7, the device 10 may be provided in the form of a handheld electronic device 32 that includes various functionalities (such as the ability to take pictures, make telephone calls, access the Internet, communicate via email, record audio and/or video, listen to music, play games, connect to wireless networks, and so forth). By way of example, the handheld device 32 may be a model of an iPod™, iPod™ Touch, or iPhone™ available from Apple Inc.

In another embodiment, the electronic device 10 may also be provided in the form of a portable multi-function tablet computing device 50, as depicted in FIG. 8. In certain embodiments, the tablet computing device 50 may provide the functionality of media player, a web browser, a cellular phone, a gaming platform, a personal data organizer, and so forth. By way of example, the tablet computing device 50 may be a model of an iPad™ tablet computer, available from Apple Inc.

While the invention has been described in terms of several embodiments, those of ordinary skill in the art will recognize that the invention is not limited to the embodiments described, but can be practiced with modification and alteration within the spirit and scope of the appended claims. The description is thus to be regarded as illustrative instead of limiting. There are numerous other variations to different aspects of the invention described above, which in the interest of conciseness have not been provided in detail. Accordingly, other embodiments are within the scope of the claims.

The invention claimed is:

1. A method of improving voice quality of a mobile device using a wireless headset with untethered earbuds comprising:

receiving a first acoustic signal from a first microphone included in a first untethered earbud and receiving a second acoustic signal from a second microphone included in a second untethered earbud;

receiving a first inertial sensor output from a first inertial sensor included in the first earbud and receiving a second inertial sensor output from a second inertial sensor included in the second earbud, wherein the first and second inertial sensors detect vibration of the user's vocal chords;

processing by the first earbud the first acoustic signal and a first noise level captured by the first microphone and processing by the second earbud the second acoustic signal and a second noise level captured by the second microphone;

processing by the first earbud the first inertial sensor output and processing by the second earbud the second inertial sensor output;

communicating the first noise level and the first and inertial sensor output from the first earbud to the second earbud;

when a) the first noise level is lower than the second noise level and b) the second inertial sensor output is less that the first inertial sensor output by a predetermined threshold, transmitting by the first earbud the first acoustic signal and the first inertial sensor output; and when a) the second noise level is lower than the first noise level and b) the first inertial sensor output is less than the second inertial sensor output by a predetermined threshold, transmitting by the second earbud the second acoustic signal and the second inertial sensor output.

2. The method of claim 1, when the first noise level is lower than the second noise level and when the first inertial sensor output is lower than the second inertial sensor output by a predetermined threshold, the method further comprising:

monitoring a first battery level of the first earbud and a second battery level of the second earbud; and transmitting by the first earbud the first acoustic signal and the first inertial sensor output when the second battery level is lower than the first battery level by a predetermined percentage threshold, and transmitting by the second earbud the second acoustic signal and the second inertial sensor output when the first battery level is lower than the second battery level by a predetermined percentage threshold.

3. The method of claim 1, further comprising:

detecting by the mobile device if the first earbud and the second earbud are in an in-ear position, and transmitting by the first earbud the first acoustic signal and the first inertial sensor output when the second earbud is not in the in-ear position, and transmitting by the second earbud the second acoustic signal and the second inertial sensor output when the first earbud is not in the in-ear position.

4. The method of claim 3, wherein detecting if the first earbud and the second earbud are in the in-ear position is based on the first inertial sensor output and the second inertial sensor output, respectively.

5. The method of claim 3, wherein the first earbud includes a pair of first microphones and the second earbud includes a pair of second microphones, wherein detecting if the first earbud is in the in-ear position is based on a power ratio between signals received from the pair of first microphones, and detecting if the second earbud is in the in-ear position is based on a power ratio between signals received from the pair of second microphones, wherein the signals received from the pair of first microphones and the signals received from the pair of second microphones are generated by the user's speech or by output from a speaker during playback.

6. The method of claim 3, wherein the first inertial sensor output includes first x, y, and z signals and the second inertial sensor output includes second x, y and z signals, wherein detecting if the first earbud and the second earbud are in the in-ear position is based on classifying a combination of the first x, y, and z signals and the second x, y, and z signals.

7. The method of claim 1, when the first earbud transmits the first acoustic signal and the first inertial sensor output, further comprising:

generating by a voice activity detector (VAD) a VAD output based on (i) the first acoustic signal and (ii) the first inertial sensor output.

8. The method of claim 7, wherein generating the VAD output comprises:

computing a power envelope of at least one of x, y, z signals generated by the first inertial sensor; and setting the VAD output to 1 to indicate that the user's voiced speech is detected if the power envelope is greater than a threshold and setting the VAD output to 0 to indicate that the user's voiced speech is not detected if the power envelope is less than the threshold.

9. The method of claim 7, wherein generating the VAD output comprises:

computing a normalized cross-correlation between any pair of x, y, z direction signals generated by the first inertial sensor;

setting the VAD output to 1 to indicate that the user's voiced speech is detected if the normalized cross-correlation is greater than a threshold, and setting the VAD output to 0 to indicate that the user's voiced speech is not detected if the normalized cross-correlation is less than the threshold.

10. The method of claim 7, wherein generating the VAD output comprises:

detecting voiced speech included in the first acoustic signal;

detecting the vibration of the user's vocal chords from the first inertial sensor output; and setting the VAD output to indicate that the user's voiced speech is detected if a coincidence of the i) detected voiced speech in the first acoustic signal and ii) the detected vibration of the user's vocal chords from the first inertial sensor output is detected and setting the VAD output to indicate that the user's voiced speech is not detected if the coincidence is not detected.

11. The method of claim 10, wherein generating the VAD output comprises:

detecting unvoiced speech by:

analyzing the first acoustic signal;

if an energy envelope in a frequency band of the first acoustic signal is greater than a threshold, a VAD output for unvoiced speech (VADu) is set to indicate that unvoiced speech is detected; and setting a global VAD output to indicate that the user's speech is detected if the voiced speech is detected or if the VADu is set to indicate that unvoiced speech is detected.

12. The method of claim 11, further comprising:

generating a pitch estimate by a pitch detector based on autocorrelation and using the output from the first inertial sensor, wherein the pitch estimate is obtained by (i) using an X, Y, or Z signal generated by the first inertial sensor that has a highest power level or (ii) using a combination of the X, Y, and Z signals generated by the first inertial sensor.

13. The method of claim 1, wherein the first inertial sensor and the second inertial sensor are accelerometers.

14. A system for improving voice quality of a mobile device comprising:

a wireless headset including a first untethered earbud and a second unthetered earbud, wherein the first earbud includes a first microphone to transmit a first acoustic signal, a first inertial sensor to generate a first inertial sensor output, a first earbud processor to process (i) a first noise level captured by the first microphone, (ii) the first acoustic signal, and (iii) the first inertial sensor output, and a first communication interface, and wherein the second earbud includes a second microphone to transmit a second acoustic signal, a second inertial sensor to generate a second inertial sensor output, a second earbud processor to process: (i) a second noise level captured by the second microphone, (ii) the second acoustic signal and (iii) the second inertial sensor output, and a second communication interface;

wherein the first and second inertial sensors detect vibration of the user's vocal chords, wherein the first communication interface is configured to communicate the first noise level and the first inertial sensor output to the second communication interface, and the second communication interface is configured to communicate the second noise level and the second inertial sensor output to the first communication interface;

wherein the first communication interface transmits the first acoustic signal and the first inertial sensor output when (i) the first noise level is lower than the second noise level, and (ii) the second inertial sensor output is lower than the first inertial sensor output by a predetermined threshold, and wherein the second communication interface transmits the second acoustic signal and the second inertial sensor output when (i) the second noise level is lower than the first noise level, and (ii) the first inertial sensor output is lower than the second inertial sensor output by a predetermined threshold.

15. The system of claim 14, wherein, when the first noise level is lower than the second noise level and when the first inertial sensor output is lower than the second inertial sensor output by a predetermined threshold, the first earbud processor monitors a first battery level of the first earbud and the second earbud processor monitors a second battery level of the second earbud; and the first communication interface transmits the first acoustic signal and the first inertial sensor output when the second battery level is lower than the first battery level by a predetermined threshold, and the second communication interface transmits the second acoustic signal and the second inertial sensor output when the first battery level is lower than the second battery level by a predetermined threshold.

16. The system of claim 14, wherein the first earbud processor and the second earbud processor detect if the first earbud and the second earbud, respectively, are in an in-ear position, and the first communication interface transmits the first acoustic signal and the first inertial sensor output when the second earbud is not in the in-ear position, and the second communication transmits the second acoustic signal and the second inertial sensor output when the first earbud is not in the in-ear position.

17. The system of claim 16, wherein detecting if the first earbud and the second earbud are in the in-ear position is based on the first inertial sensor output and the second inertial sensor output, respectively.

18. The system of claim 16, wherein the first earbud includes a pair of first microphones and the second earbud includes a pair of second microphones, wherein the first earbud processor is to detect if the first earbud is in the in-ear position based on a power ratio between signals received from the pair of first microphones, and the second earbud processor is to detect if the second earbud is in the in-ear position based on a power ratio between signals received from the pair of second microphones, wherein the signals received from the pair of first microphones and the signals received from the pair of second microphones are generated by the user's speech or by output from a speaker during playback.

19. The system of claim 16, wherein the first inertial sensor output includes first x, y, and z signals and the second inertial sensor output includes second x, y and z signals, wherein the first earbud processor and the second earbud processor detecting if the first earbud and the second earbud, respectively, are in the in-ear position is based on classifying a combination of the first x, y, and z signals and the second x, y, and z signals.

20. The system of claim 14, when the first communication interface transmits the first acoustic signal and the first inertial sensor output, the system further comprising:

a voice activity detector (VAD) to generate a VAD output based on (i) the first acoustic signal and (ii) the first inertial sensor output.

21. The system of claim 20, wherein the VAD is to compute a power envelope of at least one of x, y, z signals generated by the first inertial sensor; and the VAD is to set the VAD output to 1 to indicate that the user's voiced speech is detected if the power envelope is greater than a threshold and set the VAD output to 0 to indicate that the user's voiced speech is not detected if the power envelope is less than the threshold.

22. The system of claim 20, the VAD is to compute a normalized cross-correlation between any pair of x, y, z direction signals generated by the first inertial sensor;

the VAD to set the VAD output to 1 to indicate that the user's voiced speech is detected if the normalized cross-correlation is greater than a threshold, and to set the VAD output to 0 to indicate that the user's voiced speech is not detected if the normalized cross-correlation is less than the threshold.

23. The system of claim 20, wherein the VAD is to:

detect voiced speech included in the first acoustic signal;

detect the vibration of the user's vocal chords from the first inertial sensor output; and set the VAD output to indicate that the user's voiced speech is detected if a coincidence of the detected voiced speech in the first acoustic signal and the detected vibration of the user's vocal chords from the first inertial sensor output is detected and set the VAD output to indicate that the user's voiced speech is not detected if the coincidence is not detected.

24. The system of claim 23, wherein the VAD is to:

detect unvoiced speech by:

analyzing the first acoustic signal;

if an energy envelope in a frequency band of the first acoustic signal is greater than a threshold, a VAD output for unvoiced speech (VADu) is set to indicate that unvoiced speech is detected; and setting a global VAD output to indicate that the user's speech is detected if the voiced speech is detected or if the VADu is set to indicate that unvoiced speech is detected.

25. The system of claim 24, further comprising:

a pitch detector to generate a pitch estimate based on autocorrelation and using the output from the first inertial sensor, wherein the pitch estimate is obtained by (i) using an X, Y, or Z signal generated by the first inertial sensor that has a highest power level or (ii) using a combination of the X, Y, and Z signals generated by the first inertial sensor.

26. The system of claim 24, wherein the first inertial sensor and the second inertial sensor are accelerometers.

27. A method of improving voice quality of a mobile device using a wireless headset with untethered earbuds comprising:

receiving a first acoustic signal from a first microphone included in a first untethered earbud and receiving a second acoustic signal from a second microphone included in a second untethered earbud;

receiving a first inertial sensor output from a first inertial sensor included in the first earbud and receiving a second inertial sensor output from a second inertial sensor included in the second earbud, wherein the first and second inertial sensors detect vibration of a user's vocal chords;

processing by the first earbud the first acoustic signal and a first noise level captured by the first microphone and processing by the second earbud the second acoustic signal and a second noise level captured by the second microphone;

processing by the first earbud the first inertial sensor output and processing by the second earbud the second inertial sensor output;

when a) the first noise level is lower than the second noise level and b) the second inertial sensor output is less that the first inertial sensor output by a predetermined threshold, transmitting by the first earbud the first acoustic signal and the first inertial sensor output; and when a) the second noise level is lower than the first noise level and b) the first inertial sensor output is less than the second inertial sensor output by a predetermined threshold, transmitting by the second earbud the second acoustic signal and the second inertial sensor output.

28. The method of claim 27, further comprising:

detecting by the mobile device if the first earbud and the second earbud are in an in-ear position, and transmitting by the first earbud the first acoustic signal and the first inertial sensor output when the second earbud is not in the in-ear position, and transmitting by the second earbud the second acoustic signal and the second inertial sensor output when the first earbud is not in the in-ear position.

* * * * *